United States Patent
Takubo et al.

(10) Patent No.: US 6,521,802 B1
(45) Date of Patent: Feb. 18, 2003

(54) PROCESS FOR PREPARING FLUORINE-CONTAINING HALOGENATED HYDROCARBON COMPOUND

(75) Inventors: Seiji Takubo, Osaka (JP); Noriaki Shibata, Osaka (JP); Tatsuo Nakada, Osaka (JP); Takashi Shibanuma, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/148,415

(22) PCT Filed: Nov. 20, 2000

(86) PCT No.: PCT/JP00/08141

§ 371 (c)(1),
(2), (4) Date: May 29, 2002

(87) PCT Pub. No.: WO00/40151

PCT Pub. Date: Jun. 7, 2001

(30) Foreign Application Priority Data

Nov. 29, 1999 (JP) .............................. 11-337759

(51) Int. Cl.⁷ .............................. C07C 17/08
(52) U.S. Cl. ....................................... 570/167
(58) Field of Search ......................... 570/167

(56) References Cited

U.S. PATENT DOCUMENTS 5,763,705 A * 6/1998 Takubo et al.
5,811,604 A * 9/1998 Benson et al.

FOREIGN PATENT DOCUMENTS

| EP | 0414370 A1 | 2/1991 |
|---|---|---|
| EP | 0424531 A1 | 5/1991 |
| JP | 63262487 A | 10/1988 |
| JP | 3169829 A | 7/1991 |
| JP | 788591 B2 | 9/1995 |
| JP | 7233102 A | 9/1995 |
| JP | 791202 B2 | 10/1995 |
| JP | 8217704 A | 8/1996 |
| JP | 10251172 A | 9/1998 |
| WO | 9601797 A1 | 1/1996 |
| WO | 9833754 A1 | 8/1998 |

* cited by examiner

Primary Examiner—Alan Siegel
(74) Attorney, Agent, or Firm—Birch, Stewart, Kolasch & Birch, LLP

(57) ABSTRACT

The present invention provides a process for preparing a fluorine-containing halogenated hydrocarbon compound by fluorinating, in a reaction field where an antimony halide compound represented by the general formula:

$$SbCl_pF_{5-p} \qquad (I)$$

wherein p is a value within a range from 0 to 2, and hydrogen fluoride and a halogenated hydrocarbon compound as a raw material exist, the halogenated hydrocarbon compound in a molar ratio of the antimony halide compound to hydrogen fluoride within a range from 40/60 to 90/10. According to this process, a fluorine-containing halogenated hydrocarbon compound (HFC), which is important as a substitute compound of CFC or HCFC, can be prepared economically advantageously with good selectivity while suppressing a corrosive action of a reaction vessel.

7 Claims, No Drawings

PROCESS FOR PREPARING FLUORINE-CONTAINING HALOGENATED HYDROCARBON COMPOUND

This application is the national phase under 35 U.S.C. § 371 of PCT International Application No. PCT/JP00/08141 which has an International filing date of Nov. 20, 2000, which designated the United States of America.

BACKGROUND OF THE INVENTION

1. Field of the Invention

The present invention generally relates to a process for preparing a fluorine-containing hydrocarbon compound such as hydrofluorocarbons (HFC).

2. Description of the Related Art

Fluorine-containing hydrocarbon compounds such as hydrofluorocarbons (HFC) are used as substitute compounds of chlorofluorocarbons (CFC) and hydrochlorofluorocarbons (HCFC) which having a strong action of depleting an ozone layer, and are important compounds used as blowing agents, coolants, cleaners or propellant which do not deplete ozone in the current industry.

It has already been known to use an antimony compound as a catalyst in the process for preparing a hydrofluorocarbon. For example, Japanese Patent Kokai Publication No. 169829/1991 discloses a process for preparing $CF_3CHCl_2$, $CF_3CHClF$ or $CF_3CHF_2$ by fluorinating $CClF_2CHCl_2$ without directly using hydrogen fluoride. Japanese Patent Kokoku Publication No. 91202/1995 discloses a process for preparing $CF_3CHCl_2$ by fluorinating $CClF_2CHCl_2$ or $CCl_2FCHCl_2$, and WO96/01797 discloses a process for preparing 1,1,1,3,3-pentafluoropropane by fluorinating 1,1,1,3,3-pentachloropropane with hydrogen fluoride in the presence of an antimony halide compound.

Although it is known that the antimony halide compound is a highly corrosive compound, none of the patent publications mentioned above refers to corrosion of a reaction apparatus or prevention of such corrosion of a reaction apparatus. According to the description of examples of these publications, the concentration of the antimony halide compound used as a catalyst is usually within a range from about 0.1 to 10 mol based on 100 mol of hydrogen fluoride, and is within a range from about 20 to 30 mol at most. However, the inventors of the present invention confirmed that, when using the antimony halide compound having a concentration within such a range as the catalyst, it exhibits a metallic corrosion action in a very high level.

As described in Japanese Patent Kokai Publication No. 169829/1991, when the fluorination is conducted only by using a fluorine atom-containing antimony halide compound in the absence of hydrogen fluoride in the system, an operation of refluorinating the consumed antimony halide compound and an apparatus therefor are required. Therefore, the process can not be said to be economically advantageous.

WO98/33754 discloses a process for fluorinating 1,1,1,3,3,3-hexachloropropane in a solvent of 1-chloro-1,1,3,3,3-pentachloropropane or 1,1,1,3,3,3-hexafluoropropane and Japanese Patent Kokai Publication No. 217704/1996 discloses a process for simultaneously fluorinating dichloromethane and 1,1,1-trichloroethane, respectively, and these publications describe that the objective compound can be obtained in a good yield and that the corrosion prevention effect of the reaction apparatus is also achieved.

However, as described in WO98/33754, the process using the product or the intermediate product as the solvent is not deemed to be economically advantageous because the volume of a reaction vessel should be increased corresponding to the increase of the amount of the solvent to be used. Furthermore, since some compound has poor compatibility with hydrogen fluoride, phase separation between the hydrogen fluoride and the solvent is likely to occur in the reaction vessel, thereby to drastically lower the reaction efficiency. Therefore, such a process is applicable to limited cases.

The process of simultaneously fluorinating dichloromethane and 1,1,1-trichloroethane described in Japanese Patent Kokai Publication No. 217704/1996 is economically disadvantageous because when any one product is required, the other product which is not necessary is prepared.

In WO98/33754 and Japanese Patent Kokai Publication No. 217704/1996, although the amount of the antimony halide compound based on hydrogen fluoride is not specifically prescribed, the amount is several mol % at most as described in examples of the former publication and there is not an example wherein the antimony halide compound is used in a high concentration. On the other hand, the latter publication describes that, since the temperature of the reaction vessel is maintained at a temperature higher than a boiling point of hydrogen fluoride under a reaction pressure, hydrogen fluoride does not exist in a liquid state in the reaction vessel. That is, this description shows that the concentration of the antimony halide compound is nearly 100 mol % based on hydrogen fluoride. The absence of hydrogen fluoride in the reaction solution is not suited to efficiently conduct the reaction because the feed of a fluorine source in the fluorination reaction is delayed.

As the corrosion-proof fluorination process, Japanese Patent Kokai Publication No. 233102/1995 discloses a process using a reaction vessel made of a fluororesin and Japanese Patent Kokoku Publication No. 88591/1995 discloses a process for lowering the corrosiveness by maintaining a water content in a raw material at a low level, respectively. However, it is not possible to provide an equipment comprising a resin-lined instrument with a heating equipment in the process using the reaction vessel made of the fluororesin described in Japanese Patent Kokai Publication No. 233102/1995 as described in the specification thereof, so that it is difficult to control the reaction temperature. In addition, the raw material is fed in a gaseous form and, therefore, a pre-heater of the raw material is required, resulting in high equipment cost. The process for maintaining the water content in the raw material at a low level described in Japanese Patent Kokoku Publication No. 88591/1995 is not deemed to be economical because dehydration of an organic material requires addition of a dehydrating agent and distillation and also dehydration of hydrogen fluoride requires electrolysis and addition of a fluorine gas, resulting in increase of the number of the steps.

It has hitherto been known that a hydrogen fluoride solution of $SbCl_pF_{5-p}$ has very high corrosiveness and the reactivity of the hydrogen fluoride solution of $SbCl_pF_{5-p}$ with respect to the reaction of fluorinating the organic material increases with the increase in concentration thereof. The commonly used concentration was within a range from 1 to 10 mol %, as disclosed in examples of WO96/01797, in view of the economical efficiency.

However, the present inventors found that, when using $SbCl_pF_{5-p}$ in a concentration, which is comparatively higher than that has hitherto been used, the corrosiveness of $SbCl_pF_{5-p}$ is lowered within a conventionally used concentration range by the same degree as in the case of a comparatively low concentration range, or a concentration lower than a lower limit in the conventionally used range. Consequently, the present invention has been completed.

SUMMARY OF THE INVENTION

An object of the present invention is to provide a process for preparing a fluorine-containing halogenated hydrocarbon compound (HFC), which is important as a substitute or an alternative compound of CFC or HCFC, economically advantageously with good selectivity while suppressing a corrosive action of a reaction vessel.

The inventors have intensively studied to achieve the object described above and devised the present invention which provides a process capable of suppressing the corrosion of a reaction vessel made of a metal while maintaining a high fluorinating ability of an antimony halide compound by using a mixture of hydrogen fluoride and an antimony halide compound, which mixture contains the antimony halide compound in a comparatively high concentration. The above mixture of the antimony halide compound and hydrogen fluoride may also be expressed that it exists in the form of a hydrogen fluoride solution containing an antimony halide compound in a high concentration at normal temperature under normal pressure.

In an aspect, the process for preparing a fluorine-containing halogenated hydrocarbon compound of the present invention is characterized by fluorinating, in a reaction field where an antimony halide compound represented by the general formula:

$$SbCl_pF_{5-p} \qquad (I)$$

wherein p is a value within a range from 0 to 2, and hydrogen fluoride and a halogenated hydrocarbon compound as a raw material exist, the halogenated hydrocarbon compound in a molar ratio of the antimony halide compound to hydrogen fluoride within a range from 40/60 to 90/10, thereby to prepare a fluorine-containing halogenated hydrocarbon compound.

Particularly, the fluorine-containing halogenated hydrocarbon compound can be prepared by bringing a mixture containing 40 to 90 mol % of the antimony halide compound and 60 to 10 mol % of hydrogen fluoride into contact with the halogenated hydrocarbon compound.

It can be considered that the antimony halide compound functions as a so-called catalyst in this process. According to the process of the present invention, there can be prepared a fluorine-containing halogenated hydrocarbon compound wherein one or more halogen atoms other than fluorine atoms in the halogenated hydrocarbon compound used as a raw material are substituted with fluorine atoms. In this case, substitutable halogen atoms are, for example, one or more halogen atoms selected from chlorine atom, bromine atom and iodine atom.

DETAILED DESCRIPTION OF THE PREFERRED EMBODIMENTS OF THE INVENTION

In the present invention, as the antimony halide compound represented by the general formula: $SbCl_pF_{5-p}$, a single compound can be used, as a matter of course, and there can also be used a mixture (or a composition) of two or more kinds of compounds having the composition represented by the above general formula. Therefore, in the case of the single compound, the value of p is an integer of 0, 1 or 2. When using the composition of two or more kinds of compounds, the value of p is within a range from 0 to 2.

The reason why the value of p was defined as described above in the present invention is based on the following fact that was found out. That is, regarding the antimony halide compound wherein the value of p is not within a range form 0 to 2, the reactivity (conversion ratio, selectivity) with respect to the above fluorination reaction is drastically lower than that of the antimony halide compound wherein the value of p is within a range from 0 to 2.

When using the antimony halide compound wherein the value of p is 3 or more, since such compound has poor reactivity, it becomes necessary to raise the reaction temperature to make up for poor reactivity. However, when the reaction temperature is raised, the reaction of chlorinating an organic material is liable to occur. As a result, antimony atoms of this compound are converted from Sb (V) to Sb (III) in a reduced valence state. Therefore, the reactivity of the fluorination reaction due to the antimony halide compound is further lowered against the intention described above. Therefore, it can be said that the value of p within a range from 0 to 2 is an essential constituent in the compound $SbCl_pF_{5-p}$ when using it as the catalyst of the fluorination reaction in the present invention.

Specifically, the antimony halide compound ($SbCl_pF_{5-p}$), which can be used in the present invention, includes at least one compound selected from the group consisting of $SbF_5$, $SbClF_4$ and $SbCl_2F_3$. When any compound among this group is used alone, the value of p is an integer of 0, 1 or 2. There can also be used, as the antimony halide compound in the present invention, a mixture (composition) which is obtained by mixing $SbCl_5$ with $SbF_5$ in a predetermined ratio and has a composition represented by the general formula: $SbCl_pF_{5-p}$. For example, a composition represented by the general formula: $SbCl_pF_{5-p}$ can be prepared by mixing 0.8 mol of $SbF_5$ with 0.2 mol of $SbCl_5$ and this composition can be used as the antimony halide compound in the present invention. There can also be used, as the antimony halide compound in the present invention, a composition which is prepared by mixing 100 to 60 mol % of $SbF_5$ with $SbCl_5$ as the balance and is represented by the formula:

$$SbCl_pF_{5-p}$$

wherein $0 \leq p \leq 2$. The antimony halide compound in the present invention can also be prepared by an already-known process of reacting $SbF_5$ with HCl, or reacting $SbCl_5$ with HF in a predetermined ratio, or reacting $SbF_3$ with $Cl_2$.

The content of $SbCl_pF_{5-p}$ in the mixture of the antimony halide compound ($SbCl_pF_{5-p}$) and hydrogen fluoride (the concentration of $SbCl_pF_{5-p}$ in a hydrogen fluoride solution of $SbCl_pF_{5-p}$ when considered as the hydrogen fluoride solution of $SbCl_pF_{5-p}$) is preferably within a range from 40 to 90 mol %, and is more preferably from 50 to 80 mol %.

The reason why the content of $SbCl_pF_{5-p}$ was defined as described above is based on the following results found out by examining the corrosiveness of $SbCl\,F_{5-p}$ as a function of the concentration of $SbCl_pF_{5-p}$ in the hydrogen fluoride solution of $SbCl_pF_{5-p}$. That is, when the concentration is within a range from 0 to 0.5 mol %, the corrosiveness is in a low level. When the concentration is within a range from 0.5 to 5 mol %, the corrosiveness is enhanced with the increase of the concentration. When concentration is within a range from 5 to 10 mol %, the corrosiveness exhibits a very high level and reaches maximum. When the concentration exceeds 10 mol % and further increases, the corrosiveness makes a sudden change and tends to be lowered. When the concentration is within a range from 10 to 40 mol %, the corrosiveness is in a comparatively high level but is gradually lowered. When the concentration is 40 mol % or more, the corrosiveness is lowered to a low level by the same degree as in the case of the concentration within a range from 0 to 0.5 mol %.

As described above, although the corrosiveness is comparatively low even when the concentration of $SbCl_pF_{5-p}$ is 0.5 mol % or less, it can not be said to be practical with respect to the fluorination reaction because of low concentration.

When the concentration of $SbCl_pF_{5-p}$ in the hydrogen fluoride of $SbCl_pF_{5-p}$ is lower than 40 mol %, the corrosiveness is rapidly enhanced. Therefore, it is not preferred. On the other hand, when the concentration is higher than 90 mol %, the reaction rate is lowered by the reduction of the fluorine content of the catalyst. Therefore, it is not preferred with respect to the fluorination reaction.

The reaction temperature in the fluorinating reaction of the halogenated hydrocarbon compound in the present invention is preferably within a range from −10 to 150° C., and more preferably from 0 to 120° C. The pressure of the reaction system is preferably within a range from 0.01 to 5 MPa, and more preferably from 0.1 to 1.2 MP.

In the process of the present invention, the hydrocarbon compound used as a raw material can be represented by the general formula:

$$C_nH_xCl_yF_z \quad (II)$$

wherein n is any integer of from 1 to 3, when n is 1, x is any integer of from 0 to 2, y is any integer of from 1 to 4, z is any integer of from 0 to 2, and x, y and z satisfy the relationship: x+y+z=4, when n is 2, x is any integer of from 0 to 3, y is any integer of from 1 to 6, z is any integer of from 0 to 3, and x, y and z satisfy the relationship: x+y+z=4 or x+y+z=6, and when n is 3, x is any integer of from 0 to 3, y is any integer of from 1 to 8, z is any integer of from 0 to 6, and x, y and z satisfy the relationship: x+y+z=6 or x+y+z=8.

When the halogenated hydrocarbon described above is applied to the process of the present invention, there can be obtained a halogenated hydrocarbon compound wherein the number of fluorine atoms in a molecule was increased by the fluorination reaction. The product obtained by the process of the present invention can be represented by the general formula:

$$C_nH_xCl_{y-a}F_{z+a} \quad (III)$$

wherein n is any integer of from 1 to 3, when n is 1, x is any integer of from 0 to 2, y is any integer of from 1 to 4, z is any integer of from 0 to 3, a is any integer of from 1 to 4, and x, y, z and a satisfy the relationships: x+y+z=4 and y≧a, when n is 2, x is any integer of from 0 to 3, y is any integer of from 1 to 6, z is any integer of from 0 to 4, a is any integer of from 1 to 6, and x, y, z and a satisfy the relationship: x+y+z=4 or x+y+z=6 and the relationship: y≧a, and when n is 3, x is any integer of from 0 to 3, y is any integer of from 1 to 8, z is any integer of from 0 to 7, a is any integer of from 1 to 8, and x, y, z and a satisfy the relationship: x+y+z=6 or x+y+z=8 and the relationship: y≧a.

Specifically, when using, as the raw material, at least one halogenated hydrocarbon compound selected from the group consisting of $CH_2Cl_2$ and $CH_2ClF$, at least one fluorine-containing halogenated hydrocarbon compound selected from the group consisting of $CH_2ClF$ and $CH_2F_2$ can be prepared.

When using, as the raw material, one or more halogenated hydrocarbon compounds selected from the group of compounds represented by the molecular formulas: $C_2Cl_4$, $C_2HCl_3$, $C_2HCl_5$, $C_2HCl_4F$, $C_2HCl_3F_2$, $C_2HCl_2F_3$, $C_2HClF_4$, $C_2H_2Cl_4$, $C_2H_2Cl_3F$, $C_2H_2Cl_2F_2$ and $C_2H_2ClF_3$, one or more fluorine-containing halogenated hydrocarbon compounds represented by the molecular formulas: $C_2HCl_4F$, $C_2HCl_3F_2$, $C_2HCl_2F_3$, $C_2HClF_4$, $C_2HF_5$, $C_2H_2Cl_3F$, $C_2H_2Cl_2F_2$, $C_2H_2ClF_3$ and $C_2H_2F_4$.

The compound as the raw material represented by the above molecular formula includes, for example, $CCl_2=CCl_2$, $CHCl_2CCl_2F$, $CHCl_2CClF_2$, $CHCl_2CF_3$, $CHClFCF_3$, $CHClFCCl_2F$, $CHClFCClF_2$, $CHF_2CCl_2F$, $CHF_2CClF_2$, $CHCl=CCl_2$, $CH_2ClCCl_2F$, $CH_2ClCClF_2$, $CH_2ClCF_3$, $CH_2FCCl_2F$ and $CH_2FCClF_2$, and the fluorine-containing halogenated hydrocarbon compound as the product represented by the above molecular formula includes $CHCl_2CCl_2F$, $CHCl_2CClF_2$, $CHCl_2CF_3$, $CHClFCF_3$, $CHClFCCl_2F$, $CHClFCClF_2$, $CHF_2CCl_2F$, $CHF_2CClF_2$, $CHF_2CF_3$, $CH_2ClCCl_2F$, $CH_2ClCClF_2$, $CH_2ClCF_3$, $CH_2FCF_3$, $CH_2FCCl_2F$, $CH_2FCClF_2$ and $CH_2FCF_3$.

When using, as the raw material, at least one compound selected from the group consisting of $CCl_3CH_2CHCl_2$, $CCl_2FCH_2CHCl_2$, $CClF_2CH_2CHCl_2$, $CF_3CH_2CHCl_2$, $CF_3CH_2CHClF$, $CCl_3CH_2CHClF$, $CCl_2FCH_2CHClF$, $CClF_2CH_2CHClF$, $CCl_3CH_2CHF_2$, $CCl_2FCH_2CHF_2$, $CClF_2CH_2CHF_2$, $CHCl_2CH=CCl_2$, $CHCl_2CH=CClF$, $CHCl_2CH=CF_2$, $CHClFCH=CCl_2$, $CHClFCH=CClF$, $CHClFCH=CF_2$, $CHF_2CH=CCl_2$, $CHF_2CH=CClF$, $CCl_3CH=CHCl$, $CCl_2FCH=CHCl$, $CClF_2CH=CHCl$, $CF_3CH=CHCl$, $CCl_3CH=CHF$, $CCl_2FCH=CHF$ and $CClF_2CH=CHF$, at least one fluorine-containing halogenated hydrocarbon compound selected from the group consisting of $CCl_2FCH_2CHCl_2$, $CClF_2CH_2CHCl_2$, $CF_3CH_2CHCl_2$, $CF_3CH_2CHClF$, $CCl_3CH_2CHClF$, $CCl_2FCH_2CHClF$, $CClF_2CH_2CHClF$, $CCl_3CH_2CHF_2$, $CCl_2FCH_2CHF_2$, $CClF_2CH_2CHF_2$, $CHCl_2CH=CClF$, $CHCl_2CH=CF_2$, $CHClFCH=CCl_2$, $CHClFCH=CClF$, $CHClFCH=CF_2$, $CHF_2CH=CCl_2$, $CHF_2CH=CClF$, $CCl_2FCH=CHCl$, $CClF_2CH=CHCl$, $CF_3CH=CHCl$, $CCl_3CH=CHF$, $CCl_2FCH=CHF$, $CClF_2CH=CHF$, $CF_3CH_2CHF_2$, $CF_3CH=CHF$ and $CHF_2CH=CF_2$ The examples described above do not limit the halogenated hydrocarbon compound, which can be applied to the process of the present invention, and any hydrocarbon compound which satisfies the conditions represented by the general formula: $C_nH_xCl_yF_z$ can be applied to the process of the present invention. As a result, a fluorine-containing halogenated hydrocarbon compound represented by the general formula: $C_nH_xCl_yF_z$ a can be obtained.

In the process of the present invention, the relationship between the antimony halide compound and the raw material, which are introduced into a reaction field and are brought into contact with each other, is as follows. In the case of the batch-wise reaction, it is advantageous to set the feed amount of the halogenated hydrocarbon compound to be substituted so that the applicable amount of F (fluorine atom) being larger than the amount of Cl (chlorine atom) of such halogenated hydrocarbon compound to be substituted. For example, since the amount of F which can be utilized from the system using 8 mol of $SbF_5$ and 2 mol of HF is 18 mol (=16 mol+2 mol), it is required to control the feed amount of the halogenated hydrocarbon compound, wherein the amount of Cl to be substituted is 1 per molecule, to 18 mol or less.

Although the content of fluorine in the antimony halide compound is reduced when the reaction proceeds, the antimony halide compound whose fluorine content was reduced can be regenerated by fluorinating with hydrogen fluoride. When the rate of the reaction of regenerating the antimony halide compound is higher than that of the main reaction (the reaction of fluorinating the halogenated hydrocarbon compound in the present invention), the antimony halide compound can be fluorinated simultaneously with the main reaction during the main reaction in the reaction field of the main reaction. In the case of the continuous reaction, the halogenated hydrocarbon compound is preferably fed so that the fluorination reaction of the antimony halide compound proceeds simultaneously. When the rate of the reaction of regenerating the antimony halide compound is lower than that of the main reaction, the fluorine content of the antimony halide compound is continuously reduced with proceeding of the main component and the reactivity of the antimony halide compound is also lowered. It is also possible to cope with the situation in such a case by separately fluorinating the antimony halide compound, the fluorine content of which was reduced.

Examples of the mode for carrying out the present invention include the followings.

As the first mode, for example, there is such a mode that a predetermined amount of a halogenated hydrocarbon compound is fed to the reaction field containing a mixture of an antimony halide compound and hydrogen fluoride in a ratio defined in the present invention and the fluorination reaction is conducted. In this case, while only the halogenated hydrocarbon compound is fed to the reaction field, the fluorination reaction of the present invention can be preferably carried out as far as the ratio of the antimony halide compound to hydrogen fluoride is within a range defined in the present invention. Therefore, this mode is suited to the case wherein the reaction is conducted batch-wise.

As the second mode, for example, there is such a mode that a predetermined amount of a halogenated hydrocarbon compound and hydrogen fluoride (and a antimony halide compound, if necessary) are fed to the reaction field containing an antimony halide compound and hydrogen fluoride, thereby to control so that the ratio of the antimony halide compound to hydrogen halide is maintained within a preferred range defined in the present invention. In this case, the ratio of the antimony halide compound and hydrogen halide, which exist in the reaction field, can be maintained at a preferred value by feeding or supplementing hydrogen fluoride being consumed with proceeding of the fluorination reaction and feeding or supplementing the antimony halide compound, if necessary. This mode is particularly suited to the system in which the reaction of regenerating the antimony halide compound as the catalyst is conducted simultaneously with the main component by feeding hydrogen fluoride. Therefore, this mode can be applied widely to a middle system between a batch-wise system and a continuous system.

As the third mode, for example, there is such a mode that after a predetermined fluorination reaction according to the first or second mode is conducted, the fluorination reaction is once stopped and hydrogen fluoride is fed to the reaction field thereby to regenerate the antimony halide compound, and then the fluorination reaction in the first or second mode is conducted again. According to this mode, the process of the present invention can be carried out without making the reaction apparatus having the fluorination reaction field to be complicated.

After the fluorination reaction in the first or second mode is conducted, the antimony halide compound, whose fluorine atom content is reduced, is transferred to a separate apparatus for regeneration, where the regeneration reaction of a catalyst compound is conducted, while the fluorination reaction in the first or second can also be conducted in the reaction apparatus having the fluorination reaction field. In this case, although the reaction apparatus becomes slightly complicated, the apparatus can be efficiently utilized by minimizing the time during which the fluorination reaction apparatus can not be used in the main reaction.

Hydrogen chloride produced during the reaction is preferably extracted from the reaction vessel. The product can be extracted during the reaction or after the completion of the reaction.

As described above, the reaction of the present invention can be conducted batch-wise or continuously. Even when using any system, the reaction product can be separated and recovered by subjecting the effluent obtained from the fluorination reaction to a suitable treatment of distillation, partition, or extraction and separation while contacting with an extractant. While the example of using the halogenated hydrocarbon compound containing only chlorine atoms as the raw material is given in the above description, the process of the present invention is not limited the example and can be applied to any case wherein the halogenated hydrocarbon compound as the raw material contains one, two or three kinds selected from the group consisting of chlorine atom, bromine atom and iodine atom. As a result, a fluorine-containing halogenated hydrocarbon compound containing a larger amount of fluorine atoms can be obtained.

As the material of the reaction apparatus, which can be used in the present invention, so-called nickel alloys containing Ni as a main component, for example, Ni, Ni—Mo, Ni—Cr, Ni—Cu, Ni—Cr—Mo and Ni—Cr—Mo—Fe—Cu alloys are preferred. Preferred examples of these alloys include alloys having the following trade names: Monel 400 (JIS NCuP), Monel 500 (JIS NCUATP), Hastelloy B-2 (JIS NM2P), Hastelloy C-22, Hastelloy C-276 (JIS NMCrP), Hastelloy G (JIS NCrFMCu1P), Inconel 600 (JIS NCF600), Inconel 625 (JIS NCF625) and Inconel 825 (JIS NCF825). Depending on the reaction temperature, a stainless steel (for example, JIS Symbol SUS 304L or SUS 316L), copper and a copper alloy can also be used.

INDUSTRIAL APPLICABILITY

According to the present invention, by fluorinating, in the reaction field where an antimony halide compound represented by the general formula:

$$SbCl_pF_{5-p} \qquad (I)$$

wherein p is a value within a range from 0 to 2, and hydrogen fluoride and a halogenated hydrocarbon compound as a raw material exist, the halogenated hydrocarbon compound in a molar ratio of the antimony halide compound to hydrogen fluoride within a range from 40/60 to 90/10, a fluorine-containing halogenated hydrocarbon compound can be prepared with good selectivity in good yield as shown in Table 1 and, furthermore, the corrosiveness to a metal can be reduced to a low level as shown in Table 2 to Table 4.

EXAMPLES

Specific examples of the present invention will be described hereinafter, but the present invention is not limited to embodiments of the following examples.

Example 1A

In a 500 ml autoclave equipped with a condenser, 216.7 9 (1.0 mol) of $SbF_5$ was charged and ice-cooled. After the interior of the autoclave was evacuated to a pressure of about 0.01 MPa and deaerated, 20 g (1.0 mol) of hydrogen fluoride was introduced and the temperature was maintained at 80° C. under autogenous pressure. The temperature of the condenser was set to 5° C. and 43.3 g (0.2 mol) of 1,1,1,3,3-pentachloropropane was charged in the autoclave over one hour. Therefore, in this example, an antimony halide compound having a composition represented by $SbF_5$ was used.

The generated gas was collected by a dry ice/acetone trap under normal pressure. The collected organic material was analyzed by gas chromatography and the yield was determined. The results are shown in Table 1.

Example 1B

In a 500 ml autoclave equipped with a condenser, 173 g (0.8 mol) of $SbF_5$ was charged and ice-cooled. After the interior of the autoclave was evacuated to a pressure of about 0.01 MPa and deaerated, 24 g (1.2 mol) of hydrogen fluoride was introduced and the temperature was maintained at 80° C. under autogenous pressure. The temperature of the condenser was set to 5° C. and 43.3 g (0.2 mol) of 1,1,1,3,3-pentachloropropane was charged in the autoclave over one hour. Therefore, in this example, an antimony halide compound having a composition represented by $SbF_5$ was used.

The generated gas was collected by a dry ice/acetone trap under normal pressure. The collected organic material was analyzed by gas chromatography and the yield was determined. The results are shown in Table 1.

Example 1C

In a 500 ml autoclave equipped with a condenser, 195 g (0.9 mol) of $SbF_5$ was charged and ice-cooled. After the interior of the autoclave was evacuated to a pressure of about 0.01 MPa and deaerated, 2 g (0.1 mol) of hydrogen fluoride was introduced and the temperature was maintained at 80° C. under autogenous pressure. The temperature of the condenser was set to 5° C. and 43.3 g (0.2 mol) of 1,1,1,3,3-pentachloropropane was charged in the autoclave over one hour. Therefore, in this example, an antimony halide compound having a composition represented by $SbF_5$ was used.

The generated gas was collected by a dry ice/acetone trap under normal pressure. The collected organic material was analyzed by gas chromatography and the yield was determined. The results are shown in Table 1.

Example 2

In a 500 ml autoclave equipped with a condenser, 173.4 g (0.8 mol) of $SbF_5$ and 59.8 g (0.2 mol) of $SbCl_5$ were charged, stirred at 80° C. for 30 minutes, and then ice-cooled. After the interior of the autoclave was evacuated to a pressure of about 0.01 MPa and deaerated, 20 g (1.0 mol) of hydrogen fluoride was introduced and the temperature was maintained at 80° C. under autogenous pressure. The temperature of the condenser was set to 5° C. and 43.3 g (0.2 mol) of 1,1,1,3,3-pentachloropropane was charged in a reaction vessel over one hour. Therefore, in this example, an antimony halide compound having a composition represented by $SbClF_4$ was prepared and used.

The generated gas was collected by a dry ice/acetone trap under normal pressure. The collected organic material was analyzed by gas chromatography and the yield was determined. The results are shown in Table 1.

Example 3

In a 500 ml autoclave equipped with a condenser, 130.0 g (0.6 mol) of $SbF_5$ and 119.6 g (0.4 mol) of $SbCl_5$ were charged, stirred at 80° C. for 30 minutes, and then ice-cooled. After the interior of the autoclave was evacuated to a pressure of about 0.01 MPa and deaerated, 20 g (1.0 mol) of hydrogen fluoride was introduced and the temperature was maintained at 80° C. under autogenous pressure. The temperature of the condenser was set to 5° C. and 43.3 g (0.2 mol) of 1,1,1,3,3-pentachloropropane was charged in a reaction vessel over one hour. Therefore, in this example, an antimony halide compound having a composition represented by $SbCl_2F_3$ was prepared and used.

The generated gas was collected by a dry ice/acetone trap under normal pressure. The collected organic material was analyzed by gas chromatography and the yield was determined. The results are shown in Table 1.

Example 4

In a 500 ml autoclave equipped with a condenser, 216.7 g (1.0 mol) of $SbF_5$ was charged and ice-cooled. After the interior of the autoclave was evacuated to a pressure of about 0.01 MPa and deaerated, 20 g (1.0 mol) of hydrogen fluoride was introduced and the temperature was maintained at 20° C. under autogenous pressure. In a reaction vessel, 43.3 g (0.2 mol) of 1,1,1,3,3-pentachloropropane was charged over one hour.

The generated gas was collected by a dry ice/acetone trap under reduced pressure (0.05 to 0.001 MPa). The collected organic material was analyzed by gas chromatography and the yield was determined. The results are shown in Table 1.

Example 5

In a 500 ml autoclave equipped with a condenser, 216.7 g (1.0 mol) of $SbF_5$ was charged and ice-cooled. After the interior of the autoclave was evacuated to a pressure of about 0.01 MPa and deaerated, 20 g (1.0 mol) of hydrogen fluoride was introduced and the temperature was maintained at 80° C. under autogenous pressure. The temperature of the condenser was set to 5° C. and 33.4 g (0.2 mol) of 1,1-dichloro-3,3,3-trifluoropropane was charged in the autoclave over one hour.

The generated gas was collected by a dry ice/acetone trap under normal pressure. The collected organic material was analyzed by gas chromatography and the yield was determined. The results are shown in Table 1.

Example 6

In a 500 ml autoclave equipped with a condenser, 216.7 g (1.0 mol) of $SbF_5$ was charged and ice-cooled. After the interior of the autoclave was evacuated to a pressure of about 0.01 MPa and deaerated, 20 g (1.0 mol) of hydrogen fluoride was introduced and the temperature was maintained at 80° C. under autogenous pressure. The temperature of the condenser was set to 5° C. and 26.1 g (0.2 mol) of (E)-1-chloro-3,3,3-trifluoro-1-propene was charged in the autoclave over one hour.

The generated gas was collected by a dry ice/acetone trap under normal pressure. The collected organic material was analyzed by gas chromatography and the yield was determined. The results are shown in Table 1.

Example 7

In a 500 ml autoclave equipped with a condenser, 216.7 g (1.0 mol) of $SbF_5$ was charged and ice-cooled. After the interior of the autoclave was evacuated to a pressure of about 0.01 MPa and deaerated, 20 g (1.0 mol) of hydrogen fluoride was introduced and the temperature was maintained at 80°

C. under autogenous pressure. The temperature of the condenser was set to 5° C. and 17 g (0.2 mol) of methylene chloride was charged in the autoclave over one hour.

The generated gas was collected by a dry ice/acetone trap under normal pressure. The collected organic material was analyzed by gas chromatography and the yield was determined. The results are shown in Table 1.

Example 8

In a 500 ml autoclave equipped with a condenser, 216.7 g (1.0 mol) of $SbF_5$ was charged and ice-cooled. After the interior of the autoclave was evacuated to a pressure of about 0.01 MPa and deaerated, 20 g (1.0 mol) of hydrogen fluoride was introduced and the temperature was maintained at 100° C. under autogenous pressure. The temperature of the condenser was set to 5° C. and 33.2 g (0.2 mol) of tetrachloroethylene and 12 g (0.6 mol) of hydrogen fluoride were charged in the autoclave over one hour, followed by continuous stirring for one hour.

The generated gas was collected by a dry ice/acetone trap under normal pressure. The collected organic material was analyzed by gas chromatography and the yield was determined. The results are shown in Table 1.

Comparative Example 1

In a 500 ml autoclave equipped with a condenser, 108.5 g (0.5 mol) of $SbF_5$ was charged and ice-cooled. After the interior of the autoclave was evacuated to a pressure of about 0.01 MPa and deaerated, 90 g (4.5 mol) of hydrogen fluoride was introduced and the temperature was maintained at 80° C. under autogenous pressure. The temperature of the condenser was set to 5° C. and 43.3 9 (0.2 mol) of 1,1,1,3,3-pentachloropropane was charged in the autoclave over one hour.

The generated gas was collected by a dry ice/acetone trap under normal pressure. The collected organic material was analyzed by gas chromatography and the yield was determined. The results are shown in Table 1.

Comparative Example 2

In a 500 ml autoclave equipped with a condenser, 21.7 g (0.1 mol) of $SbF_5$ was charged and ice-cooled. After the interior of the autoclave was evacuated to a pressure of about 0.01 MPa and deaerated, 198 g (9.9 mol) of hydrogen fluoride was introduced and the temperature was maintained at 80° C. under autogenous pressure. The temperature of the condenser was set to 5° C. and 43.3 g (0.2 mol) of 1,1,1,3,3-pentachloropropane was charged in the autoclave over one hour.

The generated gas was collected by a dry ice/acetone trap under normal pressure. The collected organic material was analyzed by gas chromatography and the yield was determined. The results are shown in Table 1.

TABLE 1

(first column)

| | Example 1A | Example 1B | Example 1C | Example 2 | Example 3 | Example 4 |
|---|---|---|---|---|---|---|
| $SbF_5$ (mol) | 1.0 | 0.8 | 0.9 | 0.8 | 0.6 | 1.0 |
| $SbCl_5$ (mol) | 0 | 0 | 0 | 0.2 | 0.4 | 0 |
| HF (mol) | 1.0 | 1.2 | 0.1 | 1.0 | 1.0 | 1.0 |
| Molar ratio of ($SbF_5$ + $SbCl_5$) to ($SbF_5$ + $SbCl_5$ + HF) (mol %) | 50.0 | 40.0 | 90.0 | 50.0 | 50.0 | 50.0 |
| Halogenated hydrocarbon as raw material (mol) | | | | | | |
| $CCl_3CH_2CHCl_2$ | 0.2 | 0.2 | 0.2 | 0.2 | 0.2 | 0.2 |
| $CF_3CH_2CHCl_2$ | | | | | | |
| $CF_3CH=CHCl$ | | | | | | |
| $CH_2Cl_2$ | | | | | | |
| $CCl_2=CCl_2$ | | | | | | |
| Reaction temperature (° C.) | 80 | 80 | 80 | 80 | 80 | 20 |
| Yield (mol %) | 95 | 95 | 94 | 94 | 94 | 97 |
| Composition of product (mol %) | | | | | | |
| $CF_3CH_2CHF_2$ | 100 | 100 | 99 | 99 | 92 | 98 |
| $CF_3CH_2CHClF$ | 0 | 0 | 1 | 1 | 5 | 1 |
| $CF_3CH_2CHCl_2$ | 0 | 0 | 0 | 0 | 3 | 1 |
| $CH_2F_2$ | | | | | | |
| $CH_2ClF$ | | | | | | |
| $CH_2Cl_2$ | | | | | | |
| $CF_3CHClF$ | | | | | | |
| $CF_3CHCl_2$ | | | | | | |
| $CClF_2CHCl_2$ | | | | | | |

(second column)

| | Example 5 | Example 6 | Example 7 | Example 8 | Comp. Example 1 | Comp. Example 2 |
|---|---|---|---|---|---|---|
| $SbF_5$ (mol) | 1.0 | 1.0 | 1.0 | 1.0 | 0.5 | 0.1 |
| $SbCl_5$ (mol) | 0 | 0 | 0 | 0 | 0 | 0 |
| HF (mol) | 1.0 | 1.0 | 1.0 | 1.0 | 4.5 | 9.9 |
| Molar ratio of ($SbF_5$ + $SbCl_5$) to | 50.0 | 50.0 | 50.0 | 50.0 | 10.0 | 1.0 |

TABLE 1-continued

| (SbF$_5$ + SbCl$_5$ + HF) (mol %) Halogenated hydrocarbon (mol) | | | | | | |
|---|---|---|---|---|---|---|
| CCl$_3$CH$_2$CHCl$_2$ | | | | | 0.2 | 0.2 |
| CF$_3$CH$_2$CHCl$_2$ | 0.2 | | | | | |
| CF$_3$CH=CHCl | | 0.2 | | | | |
| CH$_2$Cl$_2$ | | | 0.2 | | | |
| CCl$_2$=CCl$_2$ | | | | 0.2 | | |
| Reaction temperature (° C.) | 80 | 80 | 80 | 100 | 80 | 80 |
| Yield (mol %) | 97 | 96 | 95 | 98 | 97 | 97 |
| Composition of product (mol %) | | | | | | |
| CF$_3$CH$_2$CHF$_2$ | 100 | 100 | | | 100 | 90 |
| CF$_3$CH$_2$CHClF | 0 | 0 | | | 0 | 4 |
| CF$_3$CH$_2$CHCl$_2$ | 0 | 0 | | | 0 | 6 |
| CH$_2$F$_2$ | | | 99 | | | |
| CH$_2$ClF | | | 1 | | | |
| CH$_2$Cl$_2$ | | | 0 | | | |
| CF$_3$CHClF | | | | 2 | | |
| CF$_3$CHCl$_2$ | | | | 95 | | |
| CClF$_2$CHCl$_2$ | | | | 3 | | |

Example 9-A1

Three metal pieces of Hastelloy C22 (about 1 cm in width, about 2.5 cm in length and about 0.3 cm in thickness), each size and weight of which were previously measured after degreasing and cleaning, were put in a 500 ml autoclave equipped with a condenser so that they are not in contact with each other. In the autoclave, a solution prepared by previously mixing 651 g (3.0 mol) of SbF$_5$ with 60 g (3.0 mol) of hydrogen fluoride was added and the solution was slowly stirred for 100 hours while maintaining at a temperature of 80° C. After the autoclave was cooled with a dry ice/acetone bath, the metal pieces were taken out from the autoclave. After the metal pieces were washed with water and dried, each weight was measured. Each corrosion rate (mm/y) of three metal pieces was calculated by applying the results of a change in weight to the following equation:

Corrosion rate (mm/y)=(87.60×x)/(d×s×t)

where x is a weight loss (mg) due to corrosion, d is a density (g/cm$^3$) of a metal piece, s is a surface area (cm$^2$) of a metal piece, and t is a test time (hr), and then an average thereof was determined and was taken as a corrosion rate of Hastelloy C22. The results are shown in Table 2.

Example 9-A2

Three metal pieces of Hastelloy C22 (about 1 cm in width, about 2.5 cm in length and about 0.3 cm in thickness), each size and weight of which were previously measured after degreasing and cleaning, were put in a 500 ml autoclave equipped with a condenser so that they are not in contact with each other. In the autoclave, a solution prepared by previously mixing 521 g (2.4 mol) of SbF$_5$ with 72 g (3.6 mol) of hydrogen fluoride was added and the solution was slowly stirred for 100 hours while maintaining at a temperature of 80° C. Thereafter, the same operation as in Example 9-A1 was conducted and the corrosion rate was determined. The results are shown in Table 2.

Example 9-B1

Three metal pieces of Hastelloy C276 (about 1 cm in width, about 2.5 cm in length and about 0.3 cm in thickness), each size and weight of which were previously measured after degreasing and cleaning, were put in a 500 ml autoclave equipped with a condenser so that they are not in contact with each other. In the autoclave, a solution prepared by previously mixing 651 g (3.0 mol) of SbF$_5$ with 60 g (3.0 mol) of hydrogen fluoride was added and the solution was slowly stirred for 100 hours while maintaining at a temperature of 80° C. Thereafter, the same operation as in Example 9-A1 was conducted and the corrosion rate was determined. The results are shown in Table 2.

Example 9-B2

Three metal pieces of Hastelloy C276 (about 1 cm in width, about 2.5 cm in length and about 0.3 cm in thickness), each size and weight of which were previously measured after degreasing and cleaning, were put in a 500 ml autoclave equipped with a condenser so that they are not in contact with each other. In the autoclave, a solution prepared by previously mixing 521 g (2.4 mol) of SbF$_5$ with 72 g (3.6 mol) of hydrogen fluoride was added and the solution was slowly stirred for 100 hours while maintaining at a temperature of 80° C. Thereafter, the same operation as in Example 9-A1 was conducted and the corrosion rate was determined. The results are shown in Table 2.

Example 9-C

In the same manner as in Example 9-A, except that Inconel 600 was used as the material of the metal pieces to be tested, each corrosion rate of Inconel 600 metal pieces was determined. The results are shown in Table 2.

Example 9-D

In the same manner as in Example 9-A, except that Monel 400 was used as the material of the metal pieces to be tested, each corrosion rate of Monel 400 metal pieces was determined. The results are shown in Table 2.

Example 9-E

In the same manner as in Example 9-A, except that stainless steel 316L was used as the material of the metal pieces to be tested, each corrosion rate of stainless steel 316L metal pieces was determined. The results are shown in Table 2.

Comparative Example 3-A

In the same manner as in Example 9-A, except that a solution containing 260.0 g (1.2 mol) of SbF$_5$ and 56 g (2.8 mol) of hydrogen fluoride was used as the solution to be charged in the autoclave, together with the metal pieces to be tested, the corrosion rate was determined. The results are shown in Table 2.

Comparative Example 3-B

In the same manner as in Example 9-B, except that a solution containing 260.0 g (1.2 mol) of $SbF_5$ and 56 g (2.8 mol) of hydrogen fluoride was used as the solution to be charged in the autoclave, together with the metal pieces to be tested, the corrosion rate was determined. The results are shown in Table 2.

Comparative Example 4-A

In the same manner as in Example 9-A, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 2.

Comparative Example 4-B

In the same manner as in Example 9-B, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 2.

Comparative Example 4-C

In the same manner as in Example 9-C, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 2.

Comparative Example 4-D

In the same manner as in Example 9-D, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 2.

Comparative Example 4-E

In the same manner as in Example 9-E, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 2.

Comparative Example 5-A

In the same manner as in Example 9-A, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 2.

Comparative Example 5-B

In the same manner as in Example 9-B, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 2.

Comparative Example 5-C

In the same manner as in Example 9-C, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 2.

Comparative Example 5-D

In the same manner as in Example 9-D, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 2.

Comparative Example 5-E

In the same manner as in Example 9-E, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 2.

TABLE 2

|  | $SbF_5$ (mol) | HF (mol) | $SbF_5/SbF_5$ + HF (mol %) | Reaction temperature (° C.) | Sample | Corrosion rate (mm/y) |
|---|---|---|---|---|---|---|
| Example 9-A1 | 3.0 | 3.0 | 50 | 80 | Hastelloy C22 | 0.05 |
| Example 9-A2 | 2.4 | 3.6 | 40 | 80 | Hastelloy C22 | 0.1 |
| Comp. Example 3-A | 1.2 | 2.8 | 30 | 80 | Hastelloy C22 | 1.0 |
| Comp. Example 4-A | 0.7 | 6.3 | 10 | 80 | Hastelloy C22 | 4.0 |
| Comp. Example 5-A | 0.1 | 9.9 | 1 | 80 | Hastelloy C22 | 2.0 |
| Example 9-B1 | 3.0 | 3.0 | 50 | 80 | Hastelloy C276 | 0.04 |
| Example 9-B2 | 2.4 | 3.6 | 40 | 80 | Hastelloy C276 | 0.08 |
| Comp. Example 3-B | 1.2 | 2.8 | 30 | 80 | Hastelloy C276 | 0.9 |
| Comp. Example 4-B | 0.7 | 6.3 | 10 | 80 | Hastelloy C276 | 4.0 |
| Comp. Example 5-B | 0.1 | 9.9 | 1 | 80 | Hastelloy C276 | 2.0 |

TABLE 2-continued

|  | $SbF_5$ (mol) | HF (mol) | $SbF_5/SbF_5 +$ HF (mol %) | Reaction temperature (° C.) | Sample | Corrosion rate (mm/y) |
| --- | --- | --- | --- | --- | --- | --- |
| Example 9-C | 3.0 | 3.0 | 50 | 80 | Inconel 600 | 0.1 |
| Comp. Example 4-C | 0.7 | 6.3 | 10 | 80 | Inconel 600 | 17 |
| Comp. Example 5-C | 0.1 | 9.9 | 1 | 80 | Inconel 600 | 6.0 |
| Example 9-D | 3.0 | 3.0 | 50 | 80 | Monel 400 | 0.1 |
| Comp. Example 4-D | 0.7 | 6.3 | 10 | 80 | Monel 400 | 15 |
| Comp. Example 5-D | 0.1 | 9.9 | 1 | 80 | Monel 400 | 5.0 |
| Example 9-E | 3.0 | 3.0 | 50 | 80 | Stainless steel 316L | 0.8 |
| Comp. Example 4-E | 0.7 | 6.3 | 10 | 80 | Stainless steel 316L | 41 |
| Comp. Example 5-E | 0.1 | 9.9 | 1 | 80 | Stainless steel 316L | 20 |

Example 10-A

The same operation as in Example 9-A was conducted, except that the temperature maintained in the step of stirring the metal pieces in the mixed solution of $SbF_5$ and hydrogen fluoride for 100 hours was changed to 20° C., the corrosion rate was determined. The results are shown in Table 3.

Example 10-B

The same operation as in Example 9-B was conducted, except that the temperature maintained in the step of stirring the metal pieces in the mixed solution of $SbF_5$ and hydrogen fluoride for 100 hours was changed to 20° C., the corrosion rate was determined. The results are shown in Table 3.

Comparative Example 6-A

In the same manner as in Example 10-A, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 3.

Comparative Example 6-B

In the same manner as in Example 10-B, except that a solution containing 151.9 g (0.7 mol) of $SbF_5$ and 126 g (6.3 mol) of hydrogen fluoride was used as the solution to be charged in the autoclave, together with the metal pieces to be tested, the corrosion rate was determined. The results are shown in Table 3.

Comparative Example 7-A

In the same manner as in Example 10-A, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 3.

Comparative Example 7-B

In the same manner as in Example 10-B, except that a solution containing 21.7 g (0.1 mol) of $SbF_5$ and 198 g (9.9 mol) of hydrogen fluoride was used as the solution to be charged in the autoclave, together with the metal pieces to be tested, the corrosion rate was determined. The results are shown in Table 3.

TABLE 3

|  | $SbF_5$ (mol) | HF (mol) | $SbF_5/SbF_5 +$ HF (mol %) | Reaction temperature (° C.) | Sample | Corrosion rate (mm/y) |
| --- | --- | --- | --- | --- | --- | --- |
| Example 10-A | 3.0 | 3.0 | 50 | 20 | Hastelloy C22 | 0.00 |
| Comp. Example 6-A | 0.7 | 6.3 | 10 | 20 | Hastelloy C22 | 1.0 |
| Comp. Example 7-A | 0.1 | 9.9 | 1 | 20 | Hastelloy C22 | 0.5 |
| Example 10-B | 3.0 | 3.0 | 50 | 20 | Hastelloy C276 | 0.00 |
| Comp. Example 6-B | 0.7 | 6.3 | 10 | 20 | Hastelloy C276 | 1.0 |
| Comp. Example 7-B | 0.1 | 9.9 | 1 | 20 | Hastelloy C276 | 0.4 |

Example 11-A

Three metal pieces of Hastelloy C22 (about 1 cm in width, about 2.5 cm in length and about 0.3 cm in thickness), each size and weight of which were previously measured after degreasing and cleaning, were put in a 500 ml autoclave equipped with a condenser so that they are not in contact with each other. In the autoclave containing the metal pieces, a solution prepared by previously mixing 520 g (2.4 mol) of SbF$_5$ with 179.4 g (0.6 mol) of SbCl$_5$, stirring at 80° for 30 minutes and adding 60 g (3.0 mol) of hydrogen fluoride was charged and the solution was slowly stirred for 100 hours while maintaining at a temperature of 20° C. Thereafter, the same operation as in Example 9-A was conducted and the corrosion rate was determined. The results are shown in Table 4.

Example 11-B

In the same manner as in Example 11-A, except that Hastelloy C276 was used as the material of the metal pieces to be tested, each corrosion rate of Hastelloy C276 metal pieces was determined. The results are shown in Table 4.

Comparative Example 8-A

In the same manner as in Example 11-A, except that a solution containing 12.1 g (0.08 mol) of SbF$_5$, 6.0 g (0.02 mol) of SbCl$_5$ and 198 g (9.9 mol) of hydrogen fluoride was used as the solution to be charged in the autoclave, together with the metal pieces to be tested, the corrosion rate was determined. The results are shown in Table 4.

Comparative Example 8-B

In the same manner as in Example 11-B, except that a solution containing 12.1 g (0.08 mol) of SbF$_5$, 6.0 g (0.02 mol) of SbCl$_5$ and 198 g (9.9 mol) of hydrogen fluoride was used as the solution to be charged in the autoclave, together with the metal pieces to be tested, the corrosion rate was determined. The results are shown in Table 4.

TABLE 4

| | SbF$_5$ (mol) | SbCl$_5$ (mol) | HF (mol) | SbF$_5$/SbF$_5$ + HF (mol %) | Reaction temperature (° C.) | Sample | Corrosion rate (mm/y) |
|---|---|---|---|---|---|---|---|
| Example 11-A | 2.4 | 0.6 | 3.0 | 50 | 20 | Hastelloy C22 | 0.00 |
| Comp. Example 8-A | 0.08 | 0.02 | 9.9 | 1 | 20 | Hastelloy C22 | 0.3 |
| Example 11-B | 2.4 | 0.6 | 3.0 | 50 | 20 | Hastelloy C276 | 0.00 |
| Comp. Example 8-B | 0.08 | 0.02 | 9.9 | 1 | 20 | Hastelloy C276 | 0.4 |

What is claimed is:

1. A process for preparing a fluorine-containing halogenated hydrocarbon compound by fluorinating, in a reaction field where an antimony halide compound represented by the general formula:

$$SbCl_pF_{5-p} \quad (I)$$

wherein p is a value within a range from 0 to 2, and hydrogen fluoride and a halogenated hydrocarbon compound as a raw material exist, said halogenated hydrocarbon compound in a molar ratio of said antimony halide compound to hydrogen fluoride within a range from 40/60 to 90/10.

2. The process according to claim 1, wherein said fluorine-containing halogenated hydrocarbon compound is prepared by bringing a mixture containing 40 to 90 mol % of said antimony halide compound and 60 to 10 mol % of hydrogen fluoride into contact with said halogenated hydrocarbon compound in said reaction field.

3. The process according to claim 1 or 2, wherein said halogenated hydrocarbon compound as said raw material and hydrogen fluoride are fed to said reaction field.

4. The process according to claim 1, wherein a halogenated hydrocarbon compound represented by the general formula:

$$C_nH_xCl_yF_z \quad (II)$$

wherein n is any integer of from 1 to 3,
when n is 1, x is any integer of from 0 to 2, y is any integer of from 1 to 4, z is any integer of from 0 to 2, and x, y and z satisfy the relationship: x+y+z=4,
when n is 2, x is any integer of from 0 to 3, y is any integer of from 1 to 6, z is any integer of from 0 t 3, and x, y and z satisfy the relationship: x+y+z=6 or x+y+z=6, and
when n is 3, x is any integer of from 0 to 3, y is any integer from 1 to 8, z is any integer from 0 to 6, and z, y and z satisfy the relationship x+y+z=8, is used as said raw material to prepare a fluorine-containing halogenated hydrocarbon compound represented by the general formula:

$$C_nH_xCl_{y-a}F_{z+a} \quad (III)$$

wherein n is any integer of from 1 to 3,
when n is 1, x is any integer of from 0 to 2, y is any integer of from 1 to 4, z is any integer of from 0 to 3, a is any integer of from 1 to 4, and x, y, z, and a satisfy the relationships: x+y+z=4 and y≧a,
when n is 2, x is any integer of from 0 to 3, y is any integer of from 1 to 6, z is any integer of from 0 to 4, a is any integer from 1 to 6, and z, y, z and a satisfy the relationship: x+y+z=4 or x+y+z=6 and the relationship: y≧a, and
when n is 3, x is any integer of from 0 to 3, y is any integer of from 1 to 8, z is any integer of from 0 to 7, a is any integer of from 1 to 8, and x, y, z and a satisfy the relationship: x+y+z=6 or x+y+z=8 and the relationship: y≧a.

5. The process according to claim 1, wherein said hologenated hydrocarbon compound used as said raw material is at least one compound selected from the group consisting of CH$_2$Cl$_2$ and CH$_2$ClF, and
at least one fluorine-containing halogenated hydrocarbon compound selected from the group consisting of CH$_2$ClF and CH$_2$F$_2$ is prepared.

6. The process according to claim 1, wherein said holgenated hydrocarbon compound used as said raw material is at least one compound selected from the group consisting of compounds represented by the molecular formulas: C$_2$Cl$_4$, C$_2$HCl$_3$, C$_2$HCl$_5$, C$_2$HCl$_4$F, C$_2$HCl$_3$F$_2$, C$_2$HCl$_2$F$_3$, C$_2$HClF$_4$, C$_2$H$_2$CH$_3$F, C$_2$H$_2$Cl$_2$F and C$_2$H$_2$ClF$_3$, and one or more fluorine-containing halogenated hydrocarbon compounds represented by the molecular formulas: $C_2HCl_4F$, $C_2HCl_3F_2$, $C_2HCl_2F_3$, $C_2HClF_4$, $C_2HF_5$, $C_2H_2Cl_3F$, $C_2H_2ClF_2$, $C_2H_2ClF_3$ and $C_2H_2F_4$ are prepared.

7. process according to claim 1,
wherein said halogenated hydrocarbon compound used as said raw material is at least one compound selected from the group consisting of $CCl_3CH_2CHCl_2$, $CCl_2FCH_2CHCl_2$, $CCl_3CH_2CHCl_2$, $CF_3CH_2CHCl_2$, $CF_3CH_2CHClF$, $CCl_3CH_2CHClF$, $CCl_2FCH_2CHClF$, $CClF_2CH_2CHClF$, $CCl_3CH_2CHF_2$, $CCl_2FCH_2CHF_2$, $CClF_2$, $CH_2CHF_2$ $CHCl_2CH=CCl_2$, $CHCl_2CH=CClF$, $CHCl_2CH=CF_2$, $CHClFCH=CCl_2$, $CHClFCH=CClF$, $CHClFCH=CF_2$, $CHF_2CH=CCl_2$, $CHF_2CH=CClF$, $CCl_3CH=CHCl$, $CCl_2FCH=CHCl$, $CClF_2CH=CHCl$, $CF_3CH=CHCl$, $CCl_3CH=CHF$, $CCl_2FCH=CHF$ and $CClF_2CH=CHF$, and at least one fluorine-containing halogenated hydrocarbon compound selected from the group consisting of $CCl_2FCH_2CHCl_2$, $CClF_2CH_2CHCl_2$, $CF_3CH_2CHCl_2$, $CF_3CH_2CHClF$, $CCl_3CH_2CHClF$, $CCl_2FCH_2CHClF$, $CClF_2CH_2CHClF$, $CCl_3CH_2CHF_2$, $CClF_2CH_2CHF_2$, $CHCl_2CH=CClF$, $CHCl_2CH=CF_2$, $CHClFCH=CCl_2$, $CHClFCH=CClF$, $CHClFCH=CF_2$, $CHF_2CH=CCl_2$, $CHF_2CH=CClF$, $CCl_2FCH=ChCl$, $CClF_2CH=CCl_2$, $CHF_2CH=CClF$, $CCl_2FCH=CHCl$, $CClF_2CH=CHCl$, $CF_3CH=CHCl$, $CCl_3CH=CHF$, $CCl_2FCH=CHF$, $CClF_2CH=CHF$, $CF_3CH_2CHF_2$, $CF_3CH=CHF$ and $CHF_2CH=CF_2$ is prepared.

* * * * *